(12) United States Patent
Khalpey et al.

(10) Patent No.: US 12,023,479 B2
(45) Date of Patent: Jul. 2, 2024

(54) PULSATILE VENTRICULAR ASSIST DEVICE

(71) Applicant: ARIZONA BOARD OF REGENTS ON BEHALF OF THE UNIVERSITY OF ARIZONA, Tucson, AZ (US)

(72) Inventors: Zain I. Khalpey, Tucson, AZ (US); Zachary David Frankman, Tucson, AZ (US); Marvin J. Slepian, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 466 days.

(21) Appl. No.: 17/058,969

(22) PCT Filed: Jun. 12, 2019

(86) PCT No.: PCT/US2019/036724
§ 371 (c)(1),
(2) Date: Nov. 25, 2020

(87) PCT Pub. No.: WO2019/241352
PCT Pub. Date: Dec. 19, 2019

(65) Prior Publication Data
US 2021/0205601 A1 Jul. 8, 2021

Related U.S. Application Data

(60) Provisional application No. 62/683,984, filed on Jun. 12, 2018.

(51) Int. Cl.
*A61M 60/279* (2021.01)
*A61M 60/161* (2021.01)
(Continued)

(52) U.S. Cl.
CPC ........ *A61M 60/279* (2021.01); *A61M 60/161* (2021.01); *A61M 60/17* (2021.01);
(Continued)

(58) Field of Classification Search
CPC .. A61M 60/279; A61M 60/843; A61M 60/17; A61M 60/161; A61M 60/295; A61M 60/837; A61M 60/508
See application file for complete search history.

(56) References Cited

U.S. PATENT DOCUMENTS

| 4,129,129 A | 12/1978 | Amrine |
| 5,147,388 A | 9/1992 | Yamazaki et al. |

(Continued)

OTHER PUBLICATIONS

Chimot et al. "Avalon Bicaval Dual-Lumen Cannula for Venovenous Extracorporeal Membrane Oxygenation: Survey of Cannula Use in France," Respiratory Support, ASAIO Journal 2013, pp. 157-161.

*Primary Examiner* — Rex R Holmes
*Assistant Examiner* — Jennifer L Ghand
(74) *Attorney, Agent, or Firm* — NGUYEN TARBET LLC

(57) ABSTRACT

A tubular pulsatile ventricular assist device (PVAD) system for providing forward flow of blood in a pulsatile, peristaltic, and non-hemolytic manner to help reduce the amount of blood clotting associated with current ventricular devices on the market. The system can encircle a portion of a blood vessel, and the system can sequentially apply a pressure through each port in a particular pre-determined patter so as to selectively occlude the lumen, thereby creating a pulsatile, peristaltic movement along a length of system. Said movement causes blood to flow through the portion of the blood vessel.

19 Claims, 7 Drawing Sheets

(51) Int. Cl.
*A61M 60/17* (2021.01)
*A61M 60/289* (2021.01)
*A61M 60/295* (2021.01)
*A61M 60/468* (2021.01)
*A61M 60/497* (2021.01)
*A61M 60/508* (2021.01)
*A61M 60/837* (2021.01)
*A61M 60/843* (2021.01)

(52) U.S. Cl.
CPC ........ *A61M 60/289* (2021.01); *A61M 60/295* (2021.01); *A61M 60/468* (2021.01); *A61M 60/497* (2021.01); *A61M 60/508* (2021.01); *A61M 60/837* (2021.01); *A61M 60/843* (2021.01); *A61M 2205/0216* (2013.01)

(56) References Cited

U.S. PATENT DOCUMENTS

| | | | |
|---|---|---|---|
| 5,222,980 A * | 6/1993 | Gealow | A61M 60/882 417/474 |
| 6,709,418 B1 | 3/2004 | Aboul-Hosn et al. | |
| 7,524,277 B1 | 4/2009 | Wang et al. | |
| 7,785,246 B2 | 12/2010 | Aboul-Hosn et al. | |
| 8,920,404 B2 | 12/2014 | Diflore et al. | |
| 9,717,830 B2 | 8/2017 | Farnan | |
| 9,782,534 B2 | 10/2017 | Kelly et al. | |
| 2005/0165269 A9 | 7/2005 | Aboul-Hosn et al. | |
| 2006/0155158 A1 | 7/2006 | Aboul-Hosn | |
| 2009/0312687 A1 | 12/2009 | Defonzo et al. | |
| 2010/0152707 A1 | 6/2010 | Morris et al. | |
| 2011/0319816 A1 | 12/2011 | von Segesser | |
| 2013/0158338 A1 | 6/2013 | Kelly et al. | |
| 2013/0218077 A1 * | 8/2013 | Cox | A61M 25/1002 604/103.01 |
| 2014/0163664 A1 * | 6/2014 | Goldsmith | A61B 17/0057 604/93.01 |
| 2014/0275724 A1 | 9/2014 | Wang et al. | |
| 2015/0223923 A1 * | 8/2015 | Forsell | A61M 60/148 600/30 |
| 2015/0224284 A1 | 8/2015 | Panotopoulos et al. | |
| 2016/0082176 A1 | 3/2016 | Kelly et al. | |
| 2016/0095972 A1 | 4/2016 | Shorey | |
| 2017/0333607 A1 | 11/2017 | Zarins | |

\* cited by examiner

PULSATILE VENTRICULAR ASSIST DEVICE

CROSS-REFERENCES TO RELATED APPLICATIONS

This application claims benefit of U.S. Provisional Patent Application No. 62/683,984 filed Jun. 12, 2018, the specification of which is incorporated herein in its entirety by reference.

BACKGROUND OF THE INVENTION

Field of the Invention

The present invention relates to a tubular pulsatile ventricular assist device (PVAD) system for providing forward flow of blood in a pulsatile, peristaltic, and non-hemolytic manner that reduces the amount of blood clotting associated with current ventricular devices on the market.

Background Art

Heart failure affects an estimated 6.6 million people in the US each year, and approximately 600,000 new diagnoses are made yearly. Heart failure can be cured with a total heart transplant. However, there is a wide gap in the number of heart organ donors available, and the number of patients who need a heart transplant. Ventricular assist devices are viewed as a viable therapy for heart failure patients and can be used as a bridge to transplant, bridge to recovery or a destination therapy for heart failure patients. Currently, there are three generations of ventricular assist devices available on the market. The first-generation ventricular assist devices are volume displacement pumps (pulsatile pumps). The second-generation ventricular assist devices are continuous flow rotary blood pumps with a contact bearing design. The third-generation ventricular assist devices are continuous flow rotary blood pumps with a noncontact bearing design.

Each succeeding generation of the ventricular assist devices have continuously aimed to address and improve limitations of the previous generation of devices, including clotting and long-term durability. While currently available ventricular assist devices have provided positive outcomes for patients, there are still a number of problems and complications associated with these devices, including bleeding, clotting and infection. The present invention provides a new system that will help decrease the amount of blood clotting associated with the current ventricular assist devices currently on the market, therefore helping to reduce clotting related conditions such as strokes and claudication.

BRIEF SUMMARY OF THE INVENTION

The present invention features a tubular pulsatile ventricular assist device (PVAD) system for providing forward flow of blood in a one-directional flow in a pulsatile, peristaltic, and non-hemolytic manner by creating various parametric movements along the length of its tubular structure. The system helps reduce the amount of blood clotting associated with current ventricular devices on the market.

In some embodiments, the system may be attached to a portion of a blood vessel such that its lumen encircles the portion of the blood vessel. The system may then sequentially apply pressure through each port using a wedge that is parametrically activated by a microcontroller such that the lumen is occluded (at least partially), thereby creating a pulsatile, peristaltic movement along the length of the system. This movement can help blood to flow through that particular portion of the blood vessel.

Without wishing to limit the present invention to any theory or mechanism, it is believed that the present invention provides clinical advantages, which may include: maintenance of red blood cell integrity, promotion of pulsatile blood flow, reduction of turbulent blood flow through the device such that shear forces are reduced, reduction of acquiring a von Willebrand Factor defect, reduction of thrombolysis and hemolysis, reduction of backflow blood regurgitation, and accommodation of blood vessel stretching. The system also provides for device sterility wherein the system does not have to make direct contact with the blood.

While the present invention will be described as being applicable to biological applications, the present invention also may be used in other fluid transport applications, for example, industrial applications, and is not limited to just biological applications.

The present invention provides pulsatile ventricular assist device (PVAD) systems. In some embodiments, the system comprises a tubular housing with a first end, a second end, an exterior surface, a shaft extending through the housing from the first end to the second end, and an interior surface lining the shaft. A membrane is disposed in the shaft of the housing, wherein the membrane is divided into at least two panels, each panel being connected to the inner surface of the housing via a seam disposed on both long edges of the membrane panel. The seam attaches to the inner surface of the housing in a manner that creates a cavity disposed between each membrane panel and the interior surface of the housing. A lumen is disposed between the panels of the membrane that can move between at least an open position and a closed position wherein the lumen is at least partially occluded. Ports extend from the exterior surface of the housing through the interior surface to the cavities, wherein the ports are arranged such that each cavity has at least two ports. An inflatable wedge extends through each port and into the respective cavity. Each inflatable wedge can be activated move between at least an expanded position and collapsed position when pressure is applied. The wedges may be activated together or in groups in in a particular pattern. When an inflatable wedge is in the expanded position, it can press against the membrane to move the membrane toward the closed position. When the inflatable wedge is in the collapsed position when pressure is removed from the wedge, the membrane can be in or move toward the open position. Each wedge can be activated in a pattern to create a peristaltic movement along a length of the membrane.

In some embodiments, the interior surface is rigid. In some embodiments, a portion of the interior surface is rigid. In some embodiments, the membrane comprises three panels and three membrane cavities. In some embodiments, the system comprises three cavities and three columns of ports, each column of ports corresponding to one cavity. In some embodiments, the system comprises at least three ports per cavity. In some embodiments, the system comprises at least four ports per cavity. In some embodiments, the ports are arranged in columns, each column corresponding to a cavity. In some embodiments, the exterior surface comprises one or more flat surfaces, each flat surface corresponding to a column of ports.

In some embodiments, the pressure to activate the wedges is air pressure. In some embodiments, the wedges are balloons. In some embodiments, the wedges are balloons having a pair of opposing pleated sides. In some embodiments, wedges that are balloons with opposing pleated sides are attached to the housing via an elastic component, wherein the elastic component helps compress and fold the wedge in the absence of pressure on the wedge. In some embodiments, the wedges of the system include at least two different wedge styles. In some embodiments, the pressure can be applied to multiple wedges that lie on a same transverse plane at the same time. In some embodiments, the pressure can be applied to multiple wedges that lie on a separate transverse plane at the same time.

In some embodiments, the system can encircle a blood vessel.

In some embodiments, the system further comprises an air pump fluidly connected to a port via a channel, the air pump functions to provide air pressure to the wedge of that port. In some embodiments, each port is fluidly connected to an air pump. In some embodiments, the system further comprises a microcontroller for operating the air pump to activate each wedge in a pre-determined pattern. In some embodiments, the microcontroller has at least one unit capable of storing and processing algorithms and mechanical instructions for operation of the system. In some embodiments, the system further comprises a pump coupled to a microcontroller for supplying air to each wedge such that peristaltic movement can be achieved. In some embodiments, the pump is an air compressor.

The present invention also features a method of pumping blood in a one directional flow in a pulsatile, peristaltic, and non-hemolytic manner. In some embodiments, the method comprises providing a system according to the present invention; attaching the system to a portion of a blood vessel, wherein the lumen encircles said portion; and sequentially applying a pressure through each port to activate a wedge, such that the membrane sequentially occludes the lumen thereby creating a pulsatile, peristaltic movement along a length of system. Said movement causes blood to flow through the portion of the blood vessel. The system of the present invention may include any of the features or combinations thereof disclosed herein.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWINGS

The features and advantages of the present invention will become apparent from a consideration of the following detailed description presented in connection with the accompanying drawings in which.

DETAILED DESCRIPTION OF THE INVENTION

Figure 1A:
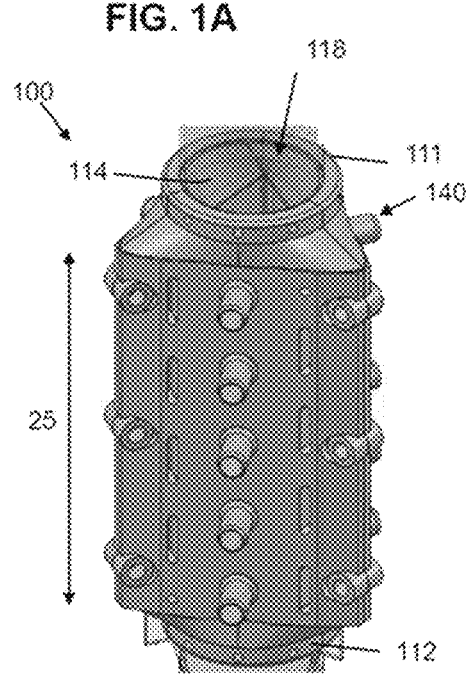
FIG. 1A shows an embodiment of the system of the present invention.
Figure 1B:
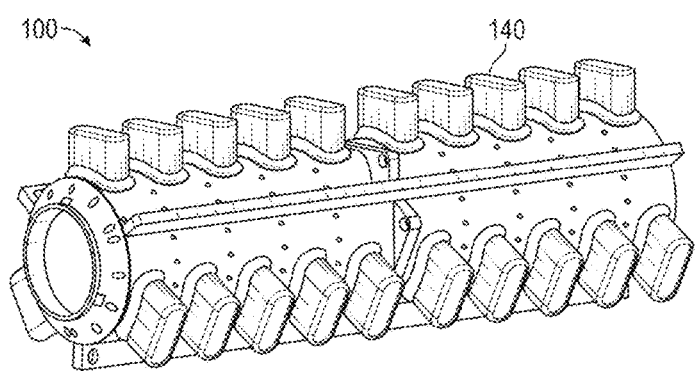
FIG. 1B shows an embodiment of the system of the present invention.

Referring now to FIG. 1A and FIG. 1B, the present invention features a tubular pulsatile ventricular assist device (PVAD) system (100). The system (100) comprises a tubular housing (110) with a first end (111), a second end (112), an exterior surface (113), a shaft (118) extending through the housing (110) from the first end (111) to the second end (112), and an interior surface (114), e.g., the lining of the shaft (118). The shaft (118) is generally hollow to at least temporarily (e.g., when not occluded) allow passage of fluid such as blood. The interior surface (114) may be generally rigid. The exterior surface (113) may be generally rigid.

As shown in FIG. 1A and FIG. 1B, the shape of the exterior surface (113) of the tubular housing (110) may be any appropriate shape, for example the exterior surface (113) may feature one or more flat surfaces or panels (e.g., three generally flat panels extending form near the first end to the second end as in FIG. 1A, e.g., a cross-sectional view of the tubular housing may be generally triangular, etc.), the exterior surface (113) may be generally rounded in shape as in FIG. 1B (e.g., a cross-sectional view of the tubular housing may be circular or similar, etc.), or the exterior surface may be any other appropriate shape. The present invention is not limited to the aforementioned examples of tubular housing shapes. In some embodiments, the exterior surface (113) has three sides, e.g., three generally flat sides. In some embodiments, the exterior surface (113) has four sides, e.g., four generally flat sides. In some embodiments, the exterior surface (113) has five sides, e.g., five generally flat sides. In some embodiments, the exterior surface (113) has more than five sides. In some embodiments, a portion of the exterior surface is curved and a portion of the exterior surface is flat.

Figure 2A:
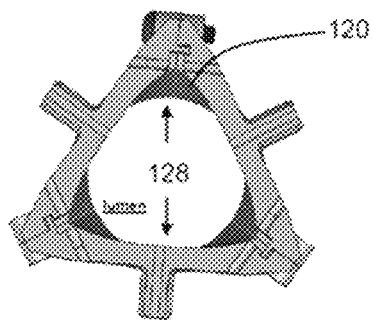
FIG. 2A shows a side cross-sectional view of the system of FIG. 1A.
Figure 2B:
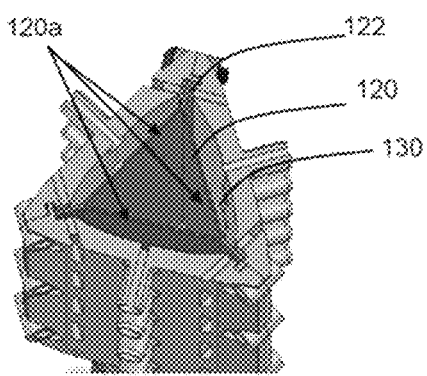
FIG. 2B shows a perspective view of the system of FIG. 2A.

Referring to FIG. 2A and FIG. 2B, the system (100) further comprises a membrane (120) disposed in the shaft (118) of the housing (110). For example, the first end of the membrane is at or near the first end (111) of the housing (110) and the second end of the membrane is at or near the second end (112) of the housing (110). The membrane (120) is shaped to appear divided into at least two panels (120a) extending the length of the housing (110). For example, the membrane (120) may be shaped to appear to comprise three panels (120a) extending the length of the housing (110), e.g., as shown in FIG. 2B. The present invention is not limited to three panels (120a). The panels (120a) of the membranes (120) may be connected to each other along their long edges, e.g., at seams (122). The panels (120a) connect to the inside surface (114) of the housing (110). Note the membrane may be one solid piece and is not limited to separate pieces connected together. The term "seam" may refer to the point of the membrane at which the long edge of one panel attaches to the inner surface of the housing or at which the long edge of the panel attaches to another long edge of a panel. The seams (122) may be extensions from the membrane. The seams (122) attach to the inner surface (114) of the housing (110). The panels of membranes (120) form a lumen (128) extending the length of the membrane (120) and housing (110). The lumen (128) can move between at least an open position for temporarily allowing passage of fluid such as blood and a closed position wherein the lumen is occluded or partially occluded and fluid cannot pass from one end of the membrane to the other. In a partially occluded state, a reduced amount of fluid can pass (as compared to the open or closed position of the membrane).

As shown in FIG. 2B, the system features membrane cavities (130), e.g., spaces between the membrane (120), the seams (122) of the membrane (120) attached to the inner surface (114) of the housing (110), and the inner surface (114) of the housing (110). Generally, there is a membrane cavity (130) or space between each panel (120a) of the membrane (120) and the inner surface (114) of the housing (110).

Also disposed in the housing, e.g., extending from the exterior surface (113) to the interior surface (114), are ports (140). The ports (40) connect the exterior surface (113) of the housing (110) to the membrane cavities (130) in the shaft (118). As shown in FIG. 1A and FIG. 1B, the housing (110) comprises columns of ports (140) wherein the ports (140) run from at or near the first end (111) to at or near the second end (112) of the housing for each membrane cavity (130). For example, FIG. 1A and FIG. 1B show three columns of ports (140) corresponding to the three membrane cavities (130). The present invention is not limited to the number of ports (140) shown in the figures. In some embodiments, each column of ports (140) has from 3 to 20 ports. For example, in some embodiments, each column of ports (140) has 3 ports. In some embodiments, each column of ports (140) has 4 ports. In some embodiments, each column of ports (140) has 5 ports. In some embodiments, each column of ports (140) has 6 ports. In some embodiments, each column of ports (140) has 7 ports. In some embodiments, each column of ports (140) has 8 ports. In some embodiments, each column of ports (140) has 9 ports. In some embodiments, each column of ports (140) has 10 ports. In some embodiments, each column of ports (140) has 11 ports. In some embodiments, each column of ports (140) has 12 ports. In some embodiments, each column of ports (140) has 13 ports. In some embodiments, each column of ports (140) has 14 ports. In some embodiments, each column of ports (140) has 15 ports. In some embodiments, each column of ports (140) has 16 ports. In some embodiments, each column of ports (140) has 17 ports. In some embodiments, each column of ports (140) has 18 ports. In some embodiments, each column of ports (140) has 19 ports. In some embodiments, each column of ports (140) has 20 ports. In some embodiments, each column of ports (140) has more than 20 ports.

Figure 10:
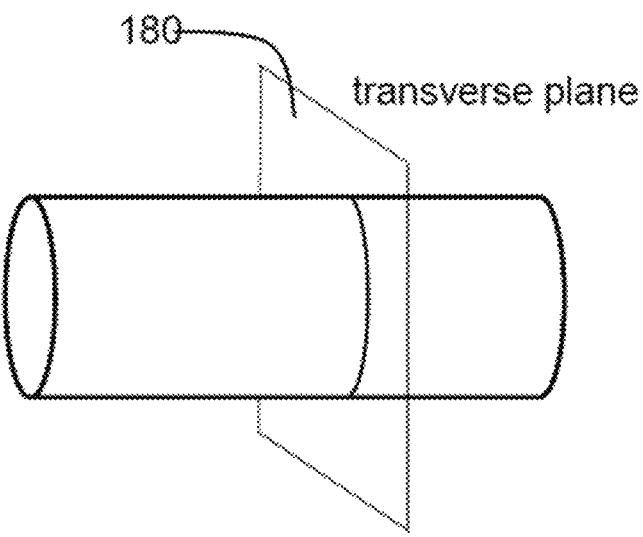
FIG. 10 shows the transverse plane along the length of the system.

As shown in FIG. 1A and FIG. 1B, the system may comprise three columns of ports, wherein the ports are spaced about 120° apart. The present invention is not limited to this configuration. In some embodiments, the system comprises two columns of ports, wherein the ports are spaced about 180° apart. In some embodiments, the system comprises four columns of ports, wherein the ports are spaced about 90° apart. In some embodiments, the ports are spaced in a staggered configuration. For example, a port or ports that lie on the same transverse plane (180) may be staggered, or misaligned, to a port or ports that lie on a separate transverse planes. The transverse plate (180) is shown in FIG. 10.

A blood vessel or other appropriate connecting tube can be encased by the housing (110). For example, with the membrane (130) in the open position, the membrane (130) can encircle the blood vessel. Pressure can be applied to the membrane (130) to move the membrane (130) to the closed position, occluding the vessel. Pressure may be applied via a mechanism that accesses the membrane cavities via each port (140). For example, in some embodiments, the system (100) comprises an inflatable wedge (150) extending from each port to its respective membrane cavity (130). The inflatable wedges (150) may operate to create a peristaltic movement along the length of the membrane (120) such that the membrane (120) occludes the lumen (128) and vessel when pressure is applied to each port (140). The inflatable wedges (150) may be inflated with air or a liquid.

Figure 3A:
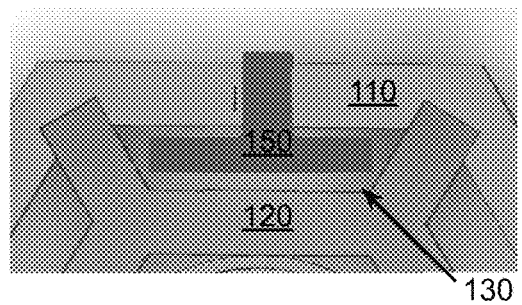
FIG. 3A shows the inflatable wedge in an uninflated state and the membrane in the open position.
Figure 3B:
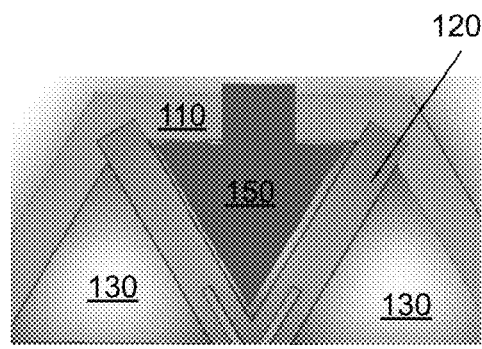
FIG. 3B shows the inflatable wedge in an inflated state and the membrane in the closed position.
Figure 4A:
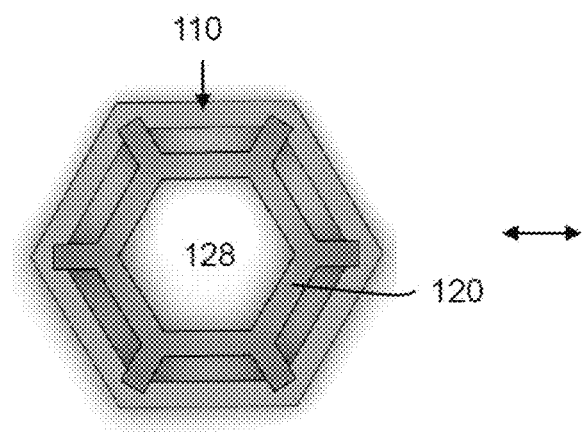
FIG. 4A shows the membrane in the open position.
Figure 4B:
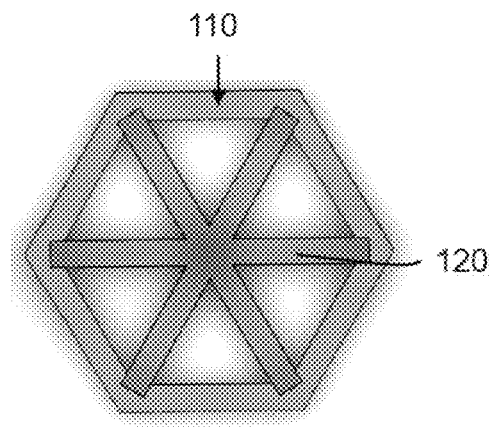
FIG. 4B shows the membrane in the closed position.
Figure 5A:
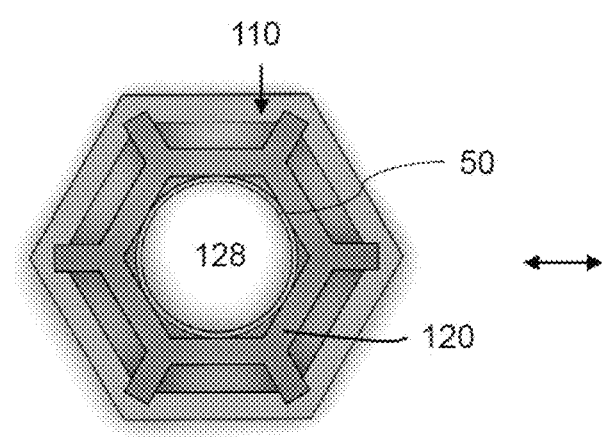
FIG. 5A shows the membrane in the open position. The system encircles a vessel.
Figure 5B:
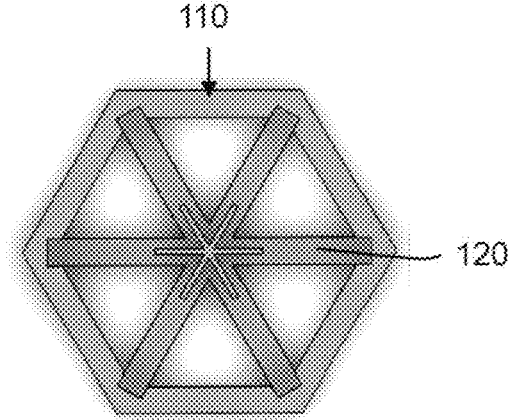
FIG. 5B shows the membrane in the closed position. The vessel encircled by the system is occluded in this state.

For example, as shown in FIG. 3A and FIG. 3B, the inflatable wedge (150) extends through the ports (140) and into the membrane cavities (130). In FIG. 3A, the membrane (120) is in the open position, allowing flow of fluid through the vessel or membrane (120). In FIG. 3B, the inflatable wedge (150) is inflated so as to move the membrane (120) to the closed position, thereby occluding the vessel. FIG. 4A and FIG. 4B shows the transition from the open lumen (FIG. 4A) to the occluded lumen (FIG. 4B). FIG. 5A and FIG. 5B shows the transition from the open lumen (FIG. 5A) with the vessel (50) therein to the occluded lumen (FIG. 5B).

Figure 6:
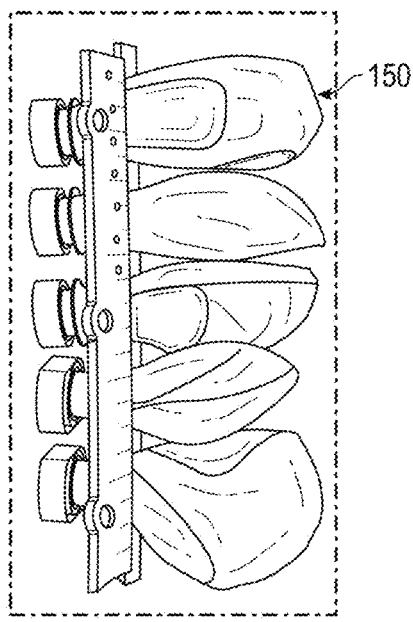
FIG. 6 shows a non-limiting example of balloon wedges.
Figure 7A:
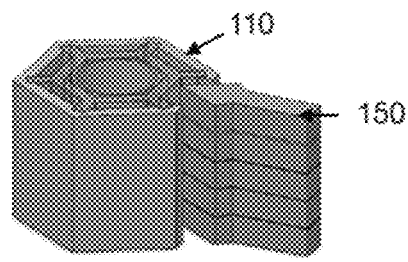
FIG. 7A shows a non-limiting example of the wedges in the form of spears. The spear version uses solenoids, pistons, or other linear actuation. Individual spears are delivered to occlude the fluid bearing tube.
Figure 7B:
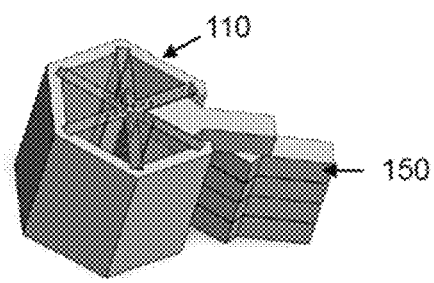
FIG. 7B shows the system of FIG. 7A. The individual spears may be activated to occlude the fluid bearing tube in a particular pattern.
Figure 8A:
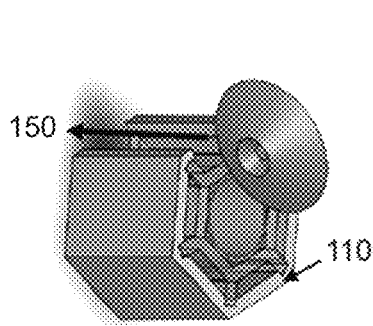
FIG. 8A shows a non-limiting example of the wedges in the form of a roller.
Figure 8B:
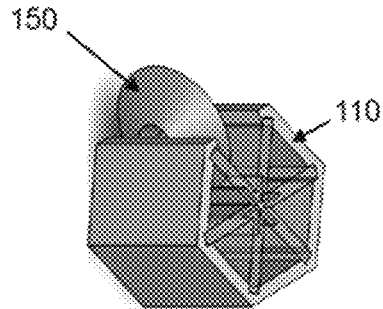
FIG. 8B shows the system of FIG. 8A. The roller version occludes the tubing as it rolls along.

Referring to FIG. 6, the inflatable wedges (150) may be balloons or bladders. As shown, the balloons extend from outside of the housing (110) and through the ports (140). The present invention is not limited to balloon-type inflatable wedges. FIG. 7A shows a non-limiting example of the wedges in the form of spears. The spear version uses solenoids, pistons, or other linear actuation. Individual spears are delivered to occlude the fluid bearing tube. FIG. 7B shows the system of FIG. 7A. The individual spears may be activated to occlude the fluid bearing tube in a particular pattern. FIG. 8A shows a non-limiting example of the wedges in the form of a roller. FIG. 8B shows the system of FIG. 8A. The roller version occludes the tubing as it rolls along.

Figure 9:
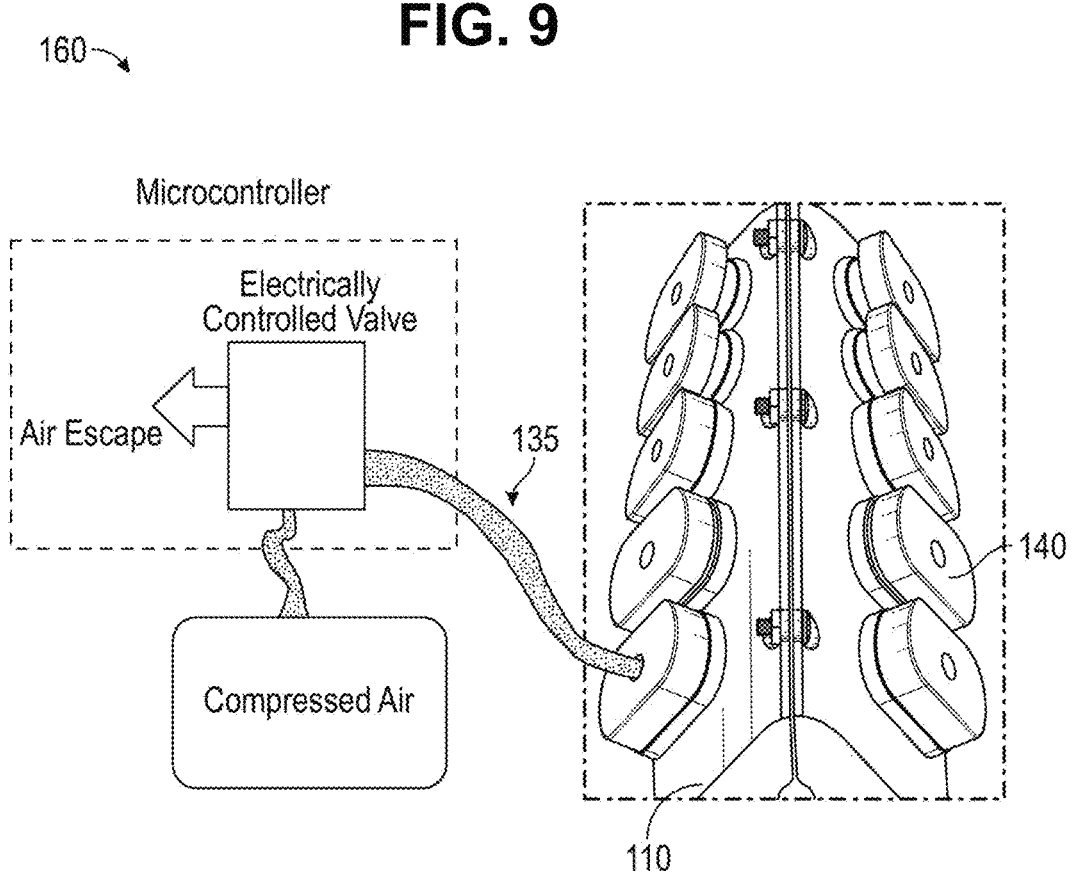
FIG. 9 shows the system operatively connected to a microcontroller with an electrically controlled valve.

FIG. 9 shows the outside of the housing (110) and the ports (140). In some embodiments, each port (140) is fluidly connected to a channel (135). The channel (135) provides a conduit through which air or liquid can be selectively moved to the inflatable wedge (150) at a desired frequency and/or pattern. FIG. 9 also shows the system (100) comprising a microcontroller (160) for operating the inflatable wedges (150). In some embodiments, the microcontroller (160) comprises an electrically controlled valve. The valve may allow for the movement of compressed air into the inflatable wedges to expand the wedges (150) and move the membrane (120) to the closed position and further to allow for the escape of air when the wedges (150) are deflated to move the membrane (120) to the open position. For example, the microcontroller (160) may activate particular wedges to achieve peristaltic and pulsatile movement. In some embodiments, the electrically controlled valve features a pump (e.g., an air compressor).

In some embodiments, the microcontroller (160) has at least one microcontroller unit capable of storing and processing algorithms and mechanical instructions for the operation of system (100). In one embodiment, the microcontroller unit can be a laptop or desktop computer connected to one or more microcontrollers actuated one or more types of wedges.

In some embodiments, the system comprises two or more different types of wedges. In some embodiments, the wedges are selected based on the size of the vessel. For example, fluid flow through larger blood vessels may utilize solid wedges actuated by solenoids, whereas fluid flow through smaller blood vessels may utilize inflatable wedges actuated by pressurized air.

In some embodiments, pressure is applied to the membrane (120), e.g., via the wedges (150), at each port (140). In some embodiments, the pressure is applied to one or more portions of the membrane (120) (via the wedges (150)) by activating the wedges at particular ports (140), e.g., using a pattern of inflation and deflation of the wedges (150).

Figure 11A:
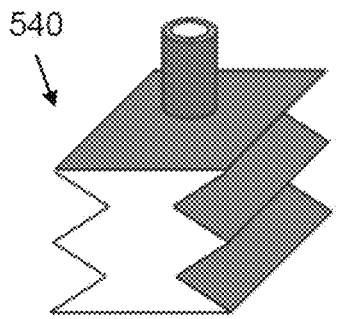
FIG. 11A shows a non-limiting example of an embodiment of the wedges, wherein the wedges are accordion-style balloons (e.g., a scaffold is folded in an accordion fashion). The accordion fold may help the balloons self-fold when deflated, e.g., in the absence of pressure.
Figure 11B:
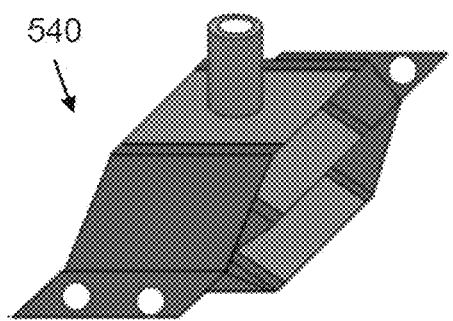
FIG. 11B shows the wedge of FIG. 11A with sides affixed to the accordion balloon.
Figure 12:
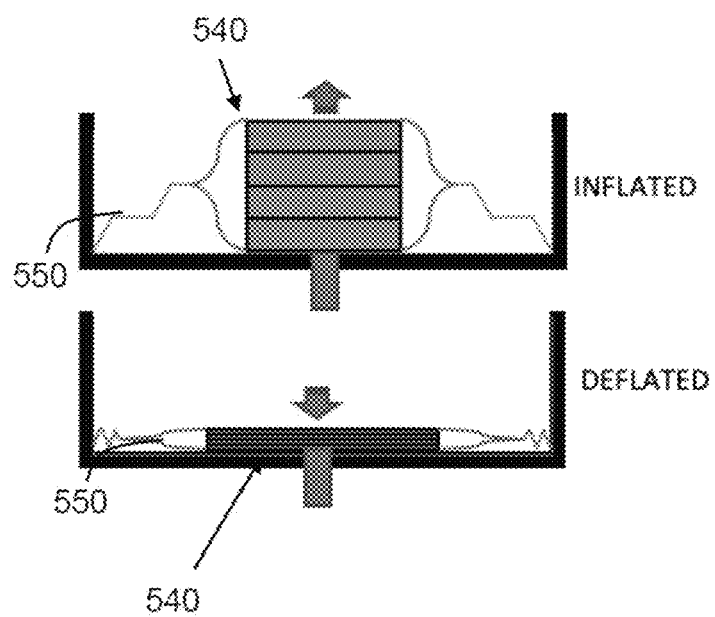
FIG. 12 shows the wedge of FIG. 11B attached to side pieces (e.g., via elastic bands, springs, etc.). The top figure shows the wedge in an inflated state and the bottom figure shows the wedge in the deflated state. The balloons self-fold once pressure is removed for repeatable actuation.

FIG. 11A, FIG. 11B, FIG. 12, FIG. 13A, FIG. 13B, FIG. 13C, FIG. 14A, and FIG. 14B show alternative embodiments of the system of the present invention and alternative embodiments of the wedges. For example, as shown in FIG. 11A, FIG. 11B, and FIG. 11C, the wedges (540) may be constructed as accordion-style or pleated balloons. For example, in some embodiments, a scaffold (such as a polystyrene polymer scaffold) is folded in an accordion or pleated fashion. An adhesive, such as but not limited to duct tape, may be used for securing the balloon in its accordion or pleated configuration. Note the channel that provides access to the interior of the balloon (e.g., where the air or liquid enters the balloon for inflating the balloon when needed). FIG. 12 shows the wedge (540) attached to side walls via a spring or elastic component (550).

Figure 14A:
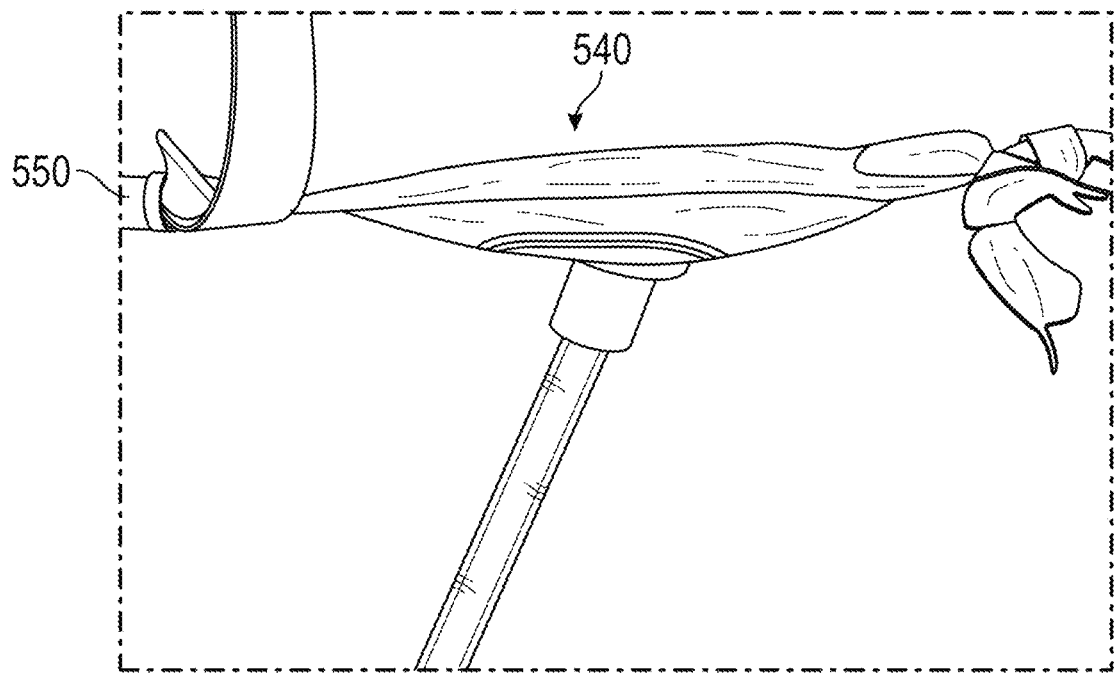
FIG. 14A shows an example of a balloon (wedge) constructed in an accordion style and attached to side walls via elastic. The balloon is in the collapsed position.
Figure 14B:
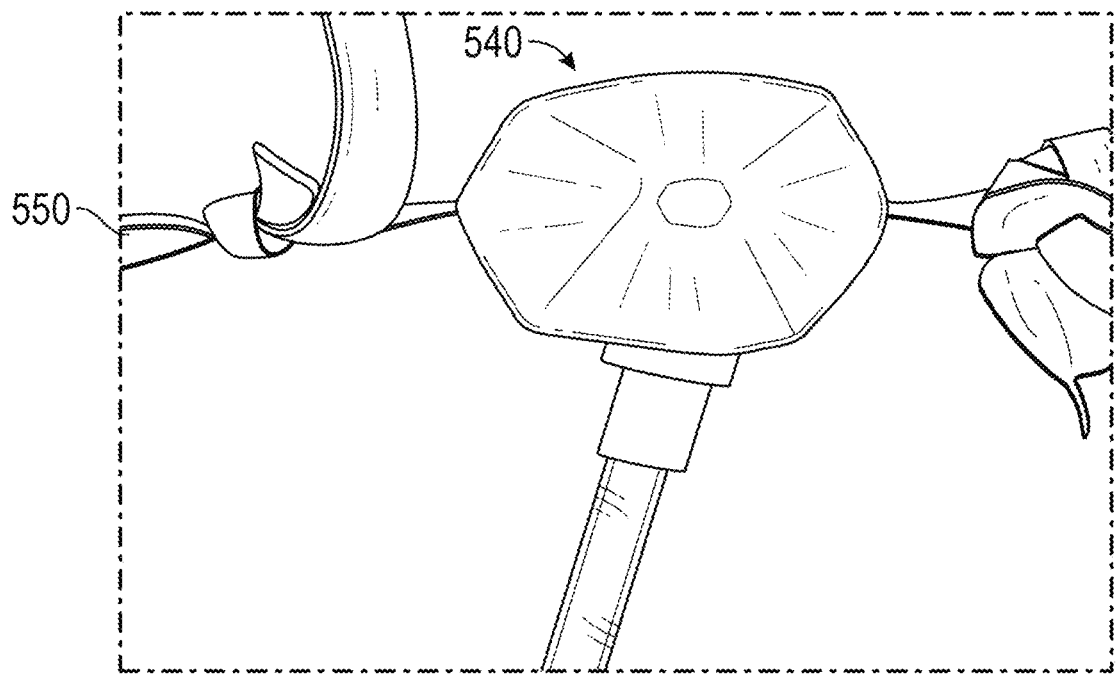
FIG. 14B shows the balloon of FIG. 14A in the expanded position after air has been pumped in. When the air pressure is released, the elastic pulls the ends of the balloons toward the side walls, helping to deflate and fold the balloon to return to its collapsed position.

As shown in FIG. 12, FIG. 14A, and FIG. 14B, the accordion or pleated fold (540) may help the balloons self-fold when deflated, e.g., in the absence of pressure. FIG. 12 shows the wedge moving between the expanded position (top panel) and collapsed position (bottom pane). FIG. 14A shows the wedge in the collapsed position, and FIG. 14B shows the wedge in the expanded position after air has been pumped in. When the air pressure is released, the elastic pulls the ends of the balloons toward the side walls, helping to deflate and fold the balloon to return to its collapsed position (e.g., the wedges may self-fold once pressure is removed for repeatable actuation).

Figure 13A:
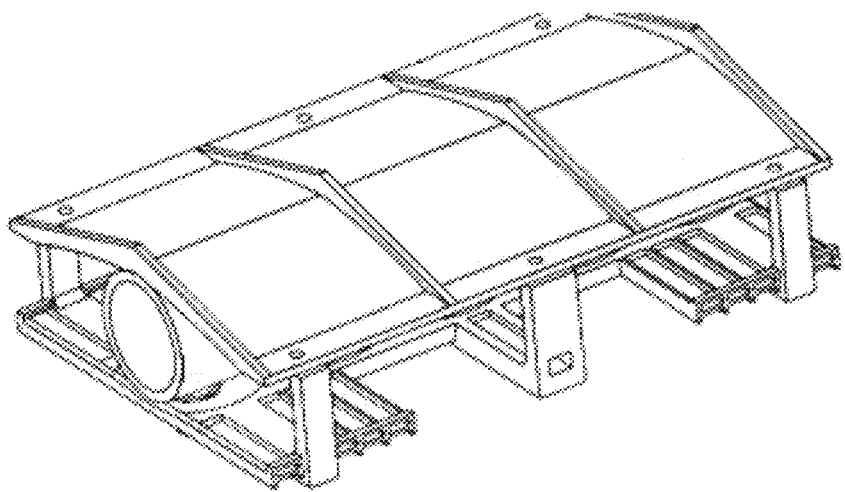
FIG. 13A shows an alternative embodiment of the system of the present invention.
Figure 13B:
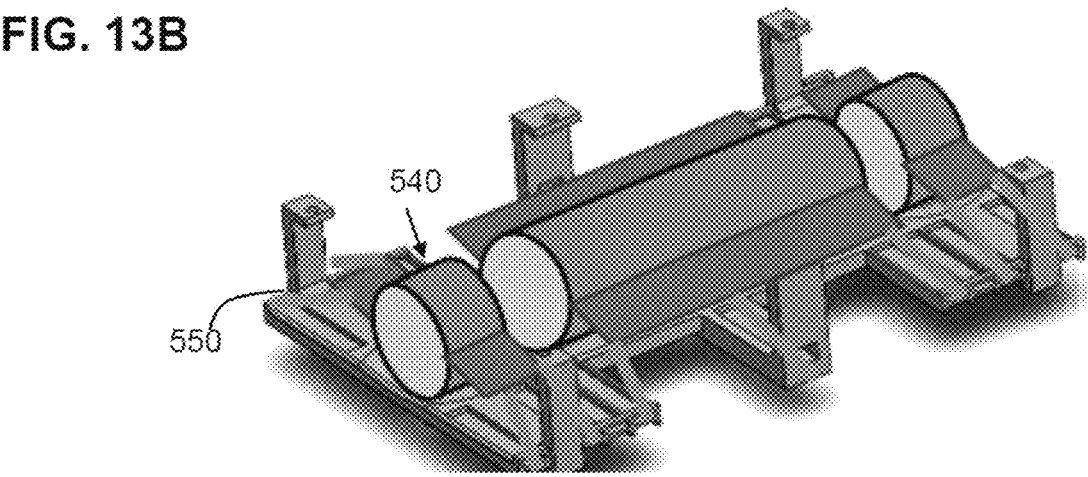
FIG. 13B shows the system of FIG. 13A. The wedges are attached to the sides via elastic bands.
Figure 13C:
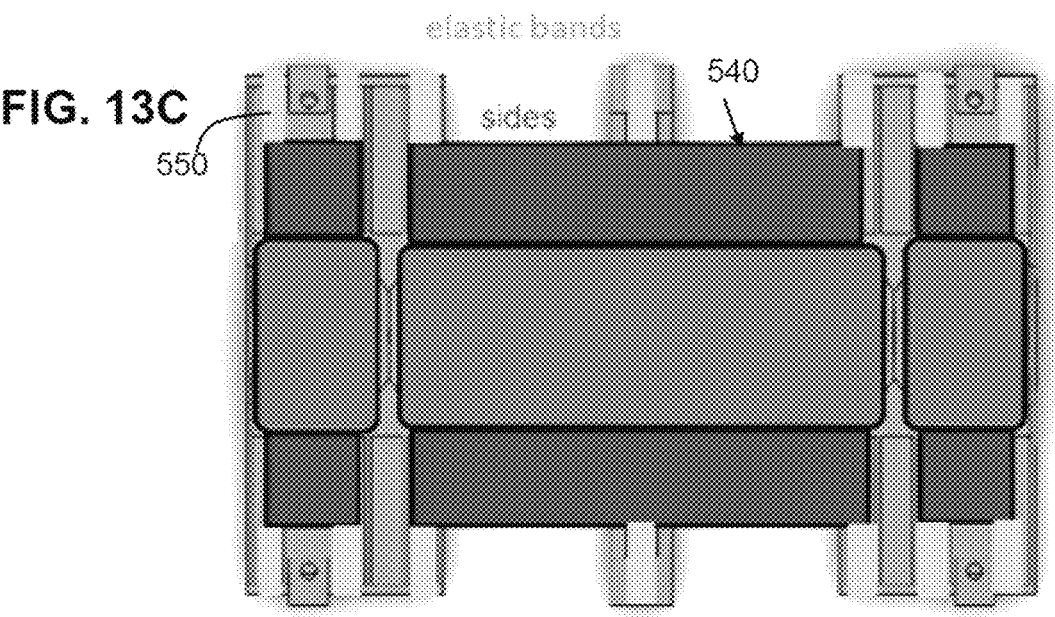
FIG. 13C shows a top view of the system of FIG. 13A and FIG. 13B. The wedges are attached to the sides via elastic bands.

FIG. 13A, FIG. 13B, and FIG. 13C show wedges (540) attached to sides via elastic bands (550). Note that in some embodiments, the wedges (540) may be different in length, e.g., the length being along the same axis as the length of the housing (110). The wedges in FIG. 13B and FIG. 13C are different in length. The present invention is not limited to any particular number of wedges or lengths of wedges.

The system (100) of the present invention is not limited to use with human vessels and may be used for any other appropriate vessels such other mammal vessels (e.g., rodent, primate, pig, etc.). Further, the system (100) of the present invention is not limited to a biological application (e.g., for use with blood vessels) and may be used in other applications to create various parametric movements along the length of the tubular structure. For example, in one embodiment, the system (100) can be used for industrial tubing, such as to drive forward movement of fluid through tubing. Tubing diameters can include, but are not limited to the standard hydraulic tubing sizes in inches: 1/8, 3/16, 1/4, 5/16, 3/8, 3/4, 7/8, 1, 1¼, 1½, 2, 2¼, 2½, 3, 3½, 4, 4½, 5, 6-10, or 10-18. The length of the system (100), e.g., the housing (110), may be any appropriate length for the application.

Non-limiting examples of ranges of the diameter of the lumen (128) may be tenths of micrometers to many hundreds of centimeters, such as 4 to 400 micrometers, 100 to 500 micrometers, 500 to 1000 micrometers, 400 to 800 micrometers, 1 to 10 mm, 1 to 25 mm, 25 to 50 mm, etc., with the tubular PVAD appropriately proportioned.

As previously discussed, the system (100) of the present invention can be used as an extra-corporeal (e.g. outside the body) pulsatile pump. In another embodiment, the system (100) can be used as an intra-corporeal (e.g. inside the body) pulsatile pump. This biocompatible system (100) achieves pulsatile one directional flow inside of the human body. The method of pumping using the system (100) is the sequential occlusion of regions of a tube to "milk" the fluid through a tube, achieving "esophageal motion" against a pressure differential. This system (100) occludes a biocompatible, flexible tube until the lumen is completely closed using a mechanism identical to that of the extra-corporeal PVAD. In some embodiments, the mechanism may be miniaturized and use solenoid actuation to occlude the lumen with a bladder-contained incompressible fluid to make battery power a possibility.

In some embodiments, physical pressure can be applied at one or more of the ports (140) at a same transverse plane (180). In an embodiment, parametric movement along the same transverse plane (180) will create a symmetrical occlusion of the lumen (128) along the transverse planes disposed along the housing (110) in a motion that minimizes fluid flow turbulence, thereby reducing the chance of throwing clots in a hemodynamic system.

Without wishing to limit the present invention to any particular mechanism or application, physical pressure applied to each port (140) along the same transverse plane (180) can be applied simultaneously, or non-simultaneously. Without wishing to limit the present invention to any particular mechanism or application, physical pressure applied to each port (140) that lies on a separate transverse plane (180) can be applied simultaneously, or non-simultaneously.

In some embodiments, this physical pressure can be applied at one or more ports (140) along a separate transverse plane (180) disposed along the length of the housing (110). In one embodiment, engagement of the flexible membrane (120) along a separate transverse plane can result in a nearly symmetrical occlusion of the lumen opening (128). In another embodiment, the engagement of the flexible membrane (120) along a separate transverse plane can result in a non-symmetrical movement, thereby create a more turbulent fluid flow, which can be beneficial in some industries, such as for the mixing of a non-homogenous fluid solution flowing through a tubular structure.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are solely for ease of examination of this patent application and are not intended in any way to limit the scope of the claims to the particular features having the corresponding reference numbers in the drawings. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

Any reference numbers recited in the below claims are solely for ease of examination of this patent application, and are exemplary, and are not intended in any way to limit the scope of the claims to the particular features having the corresponding reference numbers in the drawings.

What is claimed is:

1. A pulsatile ventricular assist device (PVAD) system (100), said system (100) comprising:
    a. a tubular housing (100) with a first end (111), a second end (112), an exterior surface (113), a shaft (118) extending through the housing (110) from the first end (111) to the second end (112), and an interior surface (114) lining the shaft (118);
    b. a membrane (120) disposed in the shaft (118) of the housing (110), the membrane (120) is divided into at least two panels (120a), each panel (120a) being connected to the interior surface (114) of the housing (110) via a seam (122) disposed on both long edges of the membrane panel (120a), the seam (122) attaches to the interior surface (114) of the housing (110) in a manner that creates a cavity (130) disposed between each membrane panel (120a) and the interior surface (114) of the housing (110), wherein a lumen (128) is disposed between the panels (120a) of the membrane (120) and configured to move between at least an open position and a closed position, wherein the lumen is at least partially occluded;
    c. ports (140) extending from the exterior surface (113) of the housing (110) through the interior surface (114) to the cavities (130), the ports (140) are arranged such that each cavity (130) has at least two ports (140); and
    d. an inflatable wedge (150) extending through each port (140) and into the respective cavity (130), each inflatable wedge (150) is configured to move between an expanded position and collapsed position, wherein when pressure is applied to the inflatable wedge (150), the inflatable wedge (150) is in the expanded position such that it presses against the membrane (120) to move the membrane (120) toward the closed position, and when pressure is removed from the inflatable wedge, the inflatable wedge (150) is in the collapsed position such that the membrane (120) moves toward or is in the open position; wherein each inflatable wedge (150) is configured to activate in a pattern to create a peristaltic movement along a length of the membrane (120).

2. The system (100) of claim 1, wherein the interior surface (114) is rigid.

3. The system (100) of claim 1, wherein a portion of the interior surface (114) is rigid.

4. The system (100) of claim 1, wherein the membrane (120) comprises three panels (120a) and three membrane cavities.

5. The system (100) of claim 1, wherein the system (100) comprises three cavities (130) and three columns of ports (140), each column of ports (140) corresponding to one cavity (130).

6. The system (100) of claim 5, wherein the system comprises at least three ports (140) per cavity (130).

7. The system (100) of claim 5, wherein the system comprises at least four ports (140) per cavity (130).

8. The system (100) of claim 1, wherein the exterior surface comprises one or more flat surfaces, each flat surface corresponding to a column of ports (140).

9. The system (100) of claim 1, wherein the pressure to activate the inflatable wedges (150) is air pressure.

10. The system (100) of claim 1, wherein the inflatable wedges (150) are balloons.

11. The system (100) of claim 1, wherein the inflatable wedges (150) are balloons having a pair of opposing pleated sides.

12. The system (100) of claim 11, wherein the inflatable wedges (150) that are balloons with opposing pleated sides are attached to the housing (110) via an elastic component (550), wherein the elastic component (550) helps compress and fold the inflatable wedges (150) in the absence of pressure on the inflatable wedges (150), wherein the elastic component (550) comprises an elastic band or a spring.

13. The system (100) of claim 1, wherein the inflatable wedges (150) of the system (100) include at least two different wedge styles.

14. The system (100) of claim 1, wherein the pressure is applied to inflatable wedges (150) that lie on a same transverse plane (180) at the same time.

15. The system (100) of claim 1, wherein the pressure is applied to inflatable wedges (150) that lie on a separate transverse plane (180) at the same time.

16. The system (100) of claim 1, wherein the system (100) is configured to encircle a blood vessel.

17. The system (100) of claim 1 further comprising an air pump fluidly connected to at least one of the ports (140) via a channel (135), the air pump functions to provide air pressure to the inflatable wedge (150) of said port (140).

18. The system (100) of claim 17, wherein each of the ports (140) is fluidly connected to the air pump.

19. The system (100) of claim 1 further comprising a pump coupled to a microcontroller for supplying air to each inflatable wedge (150) such that peristaltic movement is achieved.

* * * * *